United States Patent [19]

Boyce et al.

[11] 4,138,402

[45] Feb. 6, 1979

[54] 3-PYRID-3-YLISOXAZOLIDINE FUNGICIDES

[75] Inventors: Clive B. C. Boyce, Herne Bay; Shirley B. Webb, Sheldwich, Faversham, both of England

[73] Assignee: Shell Oil Company, Houston, Tex.

[21] Appl. No.: 830,953

[22] Filed: Sep. 6, 1977

Related U.S. Application Data

[63] Continuation-in-part of Ser. No. 717,803, Aug. 26, 1976, Pat. No. 4,066,770.

[51] Int. Cl.² ............................................. C07D 413/02
[52] U.S. Cl. .................................... 546/275; 424/263; 546/270
[58] Field of Search .......................... 260/296 R, 307 H

[56] References Cited

U.S. PATENT DOCUMENTS

| | | | |
|---|---|---|---|
| 3,849,423 | 11/1974 | Krumkalus et al. | 260/269 R X |
| 3,896,140 | 7/1975 | Plepys et al. | 260/307 H |
| 3,923,825 | 12/1975 | Quadbeck-Seeger et al. | 260/307 H |
| 3,935,219 | 1/1976 | Feuer et al. | 260/307 H |
| 4,066,770 | 1/1978 | Boyce et al. | 424/263 |

OTHER PUBLICATIONS

Paul et al., Bull. Soc. Chim. France 1967, No. 11, pp. 4179 to 4183.
Freer et al., J. of Economic Entomology, vol. 40, pp. 736 to 741 (1947).

*Primary Examiner*—John D. Randolph

[57] ABSTRACT

Certain 3-pyrid-3-yl-2-phenylisoxazolidines, useful as fungicides.

4 Claims, No Drawings

3-PYRID-3-YLISOXAZOLIDINE FUNGICIDES

This application is a continuation-in-part of application Ser. No. 717,803, filed Aug. 26, 1976, issued on Jan. 3, 1978 as U.S. Pat. No. 4,066,770.

DESCRIPTION OF THE INVENTION

It has been found that useful fungicidal properties are possessed by 3-pyrid-3-yl-2-phenylisoxazolidines of the general formula

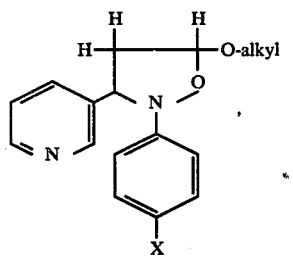

wherein X is chlorine, bromine or fluorine, and the alkyl moiety contains from one to six carbon atoms and is of straight-chain or branched-chain configuration.

It will be appreciated that these compounds contain two asymmetric carbon atoms, at the 3- and 5- positions in the heterocyclic ring and hence these compounds can exist in a number of different geometric and optical isomeric forms. All such geometric and optical isomers, together with physical and racemic mixtures of these isomers, are included within the scope of this invention.

2-Phenyl-3-(3-pyridyl)-5-ethoxyisoxazolidine (Formula I, alkyl=ethoxy) X=H is a known compound: Raymond Paul et al., Bulletin de la Société Chimique de France, 1967, pp. 4179–4183.

The isoxazolidines of the invention may be prepared by treating a nitrone of the formula

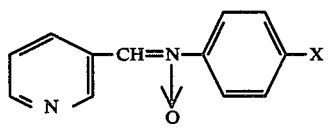 (II)

with an olefin of the formula

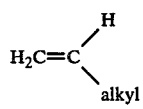 (III)

wherein X and "alkyl" have the meanings defined hereinbefore. The nitrone starting material may be prepared by suitable adaptation of known procedures (e.g. as described by Raymond Paul et al., supra). Suitably the reaction can be carried out by refluxing the reactants in an inert solvent, such as benzene, for an appropriate length of time.

These isoxazolidines have been found to be effective fungicides. Accordingly, this invention provides fungicidal compositions comprising one or more of the compounds defined in Formula I, together with a carrier and/or a surface-active agent.

The invention also includes a method of protecting crops from attack by fungi, in which crops subject to or subjected to such attack, seeds of such crops or soil in which such crops are growing or are to be grown are treated with a fungicidally effective amount of a composition containing one or more of the compounds defined in Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling. The carrier may be a solid or a fluid. Any of the materials usually applied in formulating pesticides may be used as the carrier.

Suitable solid carriers are natural and synthetic clays and silicates, for example natural silicas such as diatomacious earths; magnesium silicates, for example, talcs; magnesium aluminum silicates, for example, attapulgites and vermiculites; aluminum silicates, for example, kaolinites, montmorillinites or aluminum silicates; elements such as for example, carbon and sulphur; natural and synthetic resins such as, for example coumarone resins, polyvinyl chloride and styrene polymers and copolymers; solid polychlorophenols; bitumen; waxes such as for example, beeswax, paraffin wax, and chlorinated mineral waxes; and solid fertilizers, for example superphosphates.

Examples of suitable fluid carriers are water, alcohols, such as for example, isopropanol; glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosine; light mineral oils; chlorinated hydrocarbons, such as for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides, fungicides, or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols and will generally contain 0.5 to 95% w, preferably 0.5 to 75% w, of toxicant. Wettable powders are usually compounded to contain 25, 50 or 75% w of toxicant and usually contain, in addition to solid carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of toxicant. Granules are usually prepared to have a size between 10 and 100 BS mesh (1.676-0.152 mm), and may be manufactured by agglomeration or impregnation techniques. Generally, granules will contain ½-25% w toxicant and 0-10% w of additives such as stabilisers, slow release modifiers and binding agents. Emulsifiable concentrates usually contain, in addition to the solvent and, when necessary, co-solvent, 10-50% w/v toxicant, 2-20% w/v emulsifiers and 0-20% w/v of appropriate additives such as stabilisers, penetrants and corrosion inhibitors. Suspension concentrates are compounded so as to obtain a stable, non-sedimenting, flowable product and usually contain 10-75% w toxicant, 0.5-15% w of dispersing agents, 0.1-10% w of suspending agents such as protective colloids and thixotropic agents, 0-10% w of appropriate additives such as defoamers, corrosion inhibitors, stabilisers, penetrants and stickers, and as carrier, water or an organic liquid in which the toxicant is substantially insoluble; certain organic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The invention is further illustrated in the following examples of individual species of the fungicides of the invention, in which the identity of each of the products was confirmed by appropriate chemical and spectral analyses.

EXAMPLE 1

2-(p-Chlorophenyl)-3-(3-pyridyl)-5-ethoxyisoxazolidine (1)

11.7 g of 3-pyridyl-N-(p-chlorophenyl)nitrone in 120 ml of benzene was azeotroped to remove water. The solution was cooled to room temperature and a solution of 7.2 g of vinyl ethyl ether in 10 ml of benzene was added. The mixture was stirred and refluxed for 48 hours. The excess ether and benzene were evaporated and the residue was triturated with 60:80 petroleum spirit. The mixture was filtered and the solid was recrystallized from 60:80 petroleum spirit to give 1, as a solid, m.p.: 81-82.5°.

EXAMPLE 2

2-(p-Fluorophenyl)-3-(3-pyridyl)-5-ethoxyisoxazolidine (2)

11.7 g of 3-pyridyl-N-(p-fluorophenyl)nitrone in 120 ml of benzene was azeotroped to remove water, cooled and 7.2 g of vinyl ethyl ether in 10 ml of benzene was added; the mixture was stirred and refluxed for 48 hours. After removal of excess vinyl ethyl ether and benzene the residue was subjected to column chromatography (using a silica gel column and diethyl ether as eluant) followed by recrystallisation from 40:60 petroleum spirit to give 2, as a solid, m.p.: 41-42° C.

EXAMPLE 3

Activity against barley powdery mildew (Erysiphe graminis)

The test measured the direct antisporulant activity of compounds applied as a foliar spray. For each compound about 40 barley seedlings were grown to the one-leaf stage in a plastic pot sterile potting compost. Inoculation was effected by dousing the leaves with conidia of *Erysiphe graminis*. 24 hours after inoculation the seedlings were sprayed with a solution of the compound in a mixture of acetone (50%), surfactant (0.054%) and water using a track sprayer. The rate of application was equivalent to 1 kilogram of active material per hectare. First assessment of disease was made 5 days after treatment, when the overall level of sporulation on treated pots was compared with that on control pots.

The extent of disease control is set out in Table II below, expressed as a control rating according to the criteria:
0 = less than 50% disease control
1 = 50-80% disease control
2 = greater than 80% disease control

EXAMPLES 4-7

The further individual species of the fungicides of the invention described in Table I were prepared by the procedures described in Examples 1 and 2. The compounds are identified by structure referring to Formula I.

Compounds 1-5 were tested as fungicides by the procedure described in Example 3. All were found to have a rating of "2", indicating greater than 80% control of the fungus.

TABLE I

| Example No. | Compound No. | Compound X | "alkyl" | b.p. (Torr.)/ m.p. (° C.) |
|---|---|---|---|---|
| 4 | 4 | F | ethyl | 101-102.5° |
| 5 | 5 | Br | ethyl | 96-97.5° |
| 6 | 6 | Cl | ethyl | 80.5-82° |
| 7 | 7 | F | ethyl | 65-67.5° |

We claim:
1. A 3-pyrid-3-ylisoxazolidine of the formula

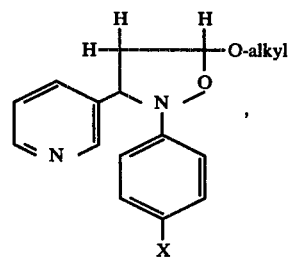

wherein X is chlorine, bromine or fluorine, and "alkyl" is alkyl of from one to six carbon atoms.

2. A compound according to claim 1 wherein $R^2$ is ethoxy and X is chlorine.

3. A compound according to claim 1 wherein $R^2$ is ethoxy and X is bromine.

4. A compound according to claim 1 wherein $R^2$ is ethoxy and X is fluorine.